(12) United States Patent
Tracey et al.

(10) Patent No.: US 6,248,356 B1
(45) Date of Patent: *Jun. 19, 2001

(54) IMMUNOTHERAPEUTIC ANTI-CANCER PHARMACEUTICAL COMPOSITIONS

(75) Inventors: Kevin J. Tracey, Greenwich, CT (US); Minghuang Zhang, Gaithersburg, MD (US)

(73) Assignee: The Picower Institut for Medical Research, Manhasset, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/874,681

(22) Filed: Jun. 13, 1997

(51) Int. Cl.⁷ ................ A61K 9/48; A61K 9/20
(52) U.S. Cl. ............ 424/464; 424/451; 424/456; 514/255; 514/256; 514/272; 514/315; 514/316; 514/340; 514/671; 514/673; 514/674
(58) Field of Search .......... 514/340, 269, 514/272, 273, 274, 255, 256, 315, 316, 318, 332, 333, 671, 673, 674; 424/451, 464, 456

(56) References Cited

U.S. PATENT DOCUMENTS 3,352,870  11/1967  Cislak et al. .......... 260/293

FOREIGN PATENT DOCUMENTS

WO 94/07489  4/1994  (WO).

OTHER PUBLICATIONS

Bair et al, (1–Prenylmethyl)amino alcohols, a new class of antitumor DNA intercalators. Discovery and initial amine side chain structure–activity studies, 1990.*
Bergeron et al. Synthetic polyamine analogues as antineoplastics. J. Med. Chem. vol. 31, pp. 1183–1190, 1988.*

* cited by examiner

Primary Examiner—Thurman K. Page
Assistant Examiner—Lakshmi Channavajjala
(74) Attorney, Agent, or Firm—Piper, Marbury, Rudnick & Wolfe, LLP; Steven B. Kelber

(57) ABSTRACT

There is disclosed a class of pharmaceutical compositions useful for the treatment of cancer, particularly solid tumors, and having a mechanism of action as spermine antagonists. The present pharmaceutical compositions are able to inhibit the inhibitory effect of spermine upon macrophage function, and thus prevent spermine-induced immunosuppression.

6 Claims, 18 Drawing Sheets

MTT Assay of C38, 91, and 94, on B16 Melenoma cells
2.5x10⁴ B16 Cells/well plated in 96-well Plates and 24 hours Treatment

SYNTHESIS OF N,N'-BIS(2,2,6,6-TETRAMETHYL-4-PIPERIDYL) HEXAMETHYLENEDIAMINE

IMMUNOTHERAPEUTIC ANTI-CANCER PHARMACEUTICAL COMPOSITIONS

TECHNICAL FIELD OF THE INVENTION

The present invention provides a class of pharmaceutical compositions useful for the treatment of cancer, particularly solid tumors, and having an immuno-modulating mechanism of action as spermine antagonists. The present pharmaceutical compositions are able to override the inhibitory effect of spermine upon tumor killing, and thus prevent spermine-induced immunosuppression.

BACKGROUND OF THE INVENTION

Anti-cancer therapy has usually followed the model wherein a cytotoxic agent is administered that kills rapidly dividing cells, which are cancer cells and some rapidly dividing host cells, such as bone marrow cells and gut epithelial cells. Thus, conventional cytotoxic cancer therapies have been limited by their side effects targeting those tissues or organs having rapidly dividing cells, (e.g., bone marrow suppression and mucositis). Advances in cancer therapies have been made to better schedule the dosing of cytotoxic agents in creative combinations and to administer growth factors that are designed to rescue host rapidly dividing cells, such as blood cell growth factors G-CSF, EPO and others.

Other approaches to cancer therapy have been to better target the cytotoxic agent to localize to the site of the tumor by antibodies, creative dosing apparatus and by a severe form of treatment, bone marrow transplantation wherein all of the rapidly dividing cells are killed and host cells needed for patient survival are replaced.

The approach of augmenting the host's immune response to a growing tumor or the presence of a tumor has been a desired approach form many years, but it has achieved limited success. For example, interleukin-2 (IL-2) is available for limited kinds of cancers but this immune activator has experienced many severe and life-threatening side effects. Other cytokines and interleukins are also being tried, yet there remains a strong need for effective and less toxic immunotherapeutic agents for cancer therapy.

Spermine and Macrophages

Under certain conditions, macrophages undergo differentiation to become capable of phagocytosis. The involvement of polyamines (of which spermine is one) in functional aspects of macrophages has been studies mainly with respect to malignant processes and treatment with inhibitors of polyamine biosynthesis. Macrophage-mediated tumorocidal activity directed against B16 melanoma cells is transiently augmented after 6 but not after 18 days of treatment with DFMO ($_\alpha$-(difluoromethyl)ornithine, an inactivator of ornithine decarboxylase (ODC); Bowlin et al., *Cancer Res.* 46:5494–5498, 1986). Treatment with Cornebacterium parvum enhanced the DFMO effect in vivo (Bowlin et al., *Cancer Immunol. Immunother.* 20:214–218, 1985) and reduced polyamine levels in macrophages, but had no effect on tumoricidal macrophage activation that can be promoted by other agents, such as $IFN_\alpha$ or $IFN_\beta$.

During the early immune response to infection or injury, macrophages synthesize pro-inflammatory cytokines which orchestrate the inflammatory reaction. Relatively small amounts of these cytokines produced locally in tissues benefit the host by activating antimicrobial pathways and stimulating tissue repair. On the other hand, if the inflammatory stimulus triggers an uncontrolled release of larger amounts of cytokines, the resulting cytokine cascade mediates the development of lethal shock and tissue injury (Tracey et al., *Science* 234:470–474, 1986; Tracey et al., *Nature* 330:662–664, 1987; and Tracey in Remnick and Friedland, eds, Tumor Necrosis Factor, Marcel Dekker, inc. 1996). This potentially disastrous scenario is normally prevented by endogenous counter-regulatory mechanisms that have evolved to inhibit cytokine over-production. One class of endogenous cytokine synthesis inhibitors are the glucocorticoid hormones, which are produced during a stress response, and suppress immune activation and cytokine synthesis (Gonzalez et al., *Infect. Immun.* 61:970–974, 1993 and Buetler et al., *Science* 232:977–980, 1986). Another class of agents is the anti-inflammatory" cytokines, consisting of IL10 and $TGF_{-\beta}$, which effectively suppress macrophage activation and pro-inflammatory cytokine synthesis (Gonzalez et al., *Infect. Immun.* 61:970–974, 1993; Tsunawaki et al., *Nature* 334:260–262, 1988; Donnelly et al., *J. Immunol.* 155:1420–1427, 1995; and Bogdan et al., *Br. J. Pharmacol.* 113:757–766, 1994). Lastly, prostaglandin E2, which accumulates at sites of inflammation, can also suppress TNF synthesis by increasing intracellular cAMP (Lehmmann et al., *J. Immunol.* 141:587–591, 1988; and Sinha et al., *Eur. J. Immunol.* 25:147–153, 1995). Together, these endogenous molecular mediators are supposed to counter-regulate or dampen the inflammatory response, and to prevent overabundant production of potentially injurious pro-inflammatory cytokines.

Spermine is a ubiquitous biogenic amine that is positively charged at physiological pH. Spermine is a ubiquitous natural polyamine that has been implicated as an inhibitor of some immune responses, including human neutrophil locomotion, T cell activity and NO production in murine macrophages. Pathological conditions, such a major injury or cancer, result in massive impairment of immunological reactivity with clinical consequences of high susceptibility towards serious infection and tumor escape from the immune system. Spermine has been widely studied for its biological roles in regulating DNA synthesis and cellular proliferation, modulation of ion channel function, and as a intracellular second messenger signaling agent (Blanchard et al., *Infect. Immun.* 55:433–437, 1987). Spermine has been implicated as an inhibitor of an immune response. For example, spermine prevents the synthesis of nitric oxide synthase and NO production in macrophages activated by bacterial endotoxin (Southan et al., *Biochem. Biophys. Res. Comm.* 203:1638–1644, 1944; and Szabe et al., *Cancer Res.* 52:1891–1894, 1992), down-regulates human neutrophil locomotion (Ferrante, *Immunol.* 54:785–790, 1985), and is immunosuppressive to T cells (Quan et al., *Am. J. Reprod. Immunol.* 22:64–69, 1990). Increased spermine levels have been measured in tissues following injury, inflammation, and infection, derived, in part, from a release of intracellular spermine from dying and injured cells. Several theories have been proposed that the accumulation of spemnine and the products of its oxidative metabolism via polyamine oxidase mediate anti-inflammatory activity found in inflammatory exudates, human pregnancy serum, plasma from arthritic rats, and human rheumatoid synovial fluid (Ferrante, *Immunol.* 54:785–790, 1985; Hempel et al., *Nature* 225:32–35, 1983; Lewis et al., *Biochem. Pharmacol.* 25:1435, 1976; Persellin, *Arthritis Rheum.* 15:144, 1972; Rinandi, *Indian J. Med. Res.* 44:144, 1956; and Robinson and Robson *Br. J. Pharmacol.* 23:420, 1964). In addition, high spermine concentrations have been found in solid tumor tissue, leading to a supposition that the spermine concentrations are secreted by tumor cells to act as an immunoprotectant mechanism against the host defense system.

One of the early cytokines discovered was tumor necrosis factor (TNF) and, as implied by its name, this cytokine was thought to be an immune effector that could lyse and kill tumor cells. Macrophages are terminally differentiated immune effector cells that, when activated, can lyse tumor cells. The macrophage lytic activity is mediated, in part, by secreting the cytokine $TNF_\alpha$. Curiously, the anti-tumor activity of macrophages is somehow suppressed during tumor growth.

The role of a macrophage, or a mononuclear phagocyte in immunology has long been recognized. Macrophages act by phagocytosis and intracellular disposal. It is a goal of cancer immunotherapy to activate macrophages, since activated macrophages have been shown to lyse tumor cells under both in vitro and in vivo conditions. Macrophages have a continuous function for removal of senescent or damaged red blood cells from the circulation, but this function is constitutive and does not require activation. By contrast, macrophages require activation to perform infrequent functions, such as participation in a host defense against cancer. By "activation" it is generally meant in the literature that an activated macrophage may mean any change in behavior of the macrophage, such as increased adherence, altered motility, increased enzymatic activity, or increased phagocytosis. There are many mechanisms that have been studied that can activate macrophages and include, for example, bacterial endotoxin, and cytokines such as TNF, GM-CSF, IL-2, IL-1 and others. Subsequent direct tumor cell lysis occurs both by direct macrophage-tumor cell contact and the release of a plethora of cytotoxic molecules from the activated macrophages (e.g., $H_2O_2$, NO, IL-1, TNF, and collagenases). The importance of direct contact of the macrophage to the tumor cell requires that the macrophage be located within or in proximity to tumor cell tissue. If there are substances secreted by tumor cells that deactivate or prevent macrophage activation, the ability to deactivate the deactivators (a double negative makes a positive) represents an important therapeutic advance for immunotherapeutic treatment of cancer.

The present invention is based upon the discovery of a group of compounds having such activity, wherein the tumor-secreted deactivating substance is spermine.

SUMMARY OF THE INVENTION

The present invention provides a pharmaceutical composition for cancer immunotherapy treatment comprising a compound selected from formula I and a pharmaceutically acceptable carrier, wherein formula I comprises:

(I)

wherein "A" is independently —$CH_2$—, —O—, —NH—, —CO—, phenyl, or pyrimidnyl;

wherein $R_1$, $R_2$, $R_3$, $R_4$, $R_5$, $R_6$, $R_7$, $R_8$, and $R_9$ are each independently H, $C_{1-6}$ alkyl, $C_{1-6}$ alkenyl, $C_{1-6}$ alkoxy, or phenyl;

wherein "X" is a linker moiety selected from the group consisting of $C_{2-10}$ alkyl, $C_{2-10}$ alkenyl, and $R_{10}$–$R_{11}$=$R_{10}$; wherein $R_{10}$ is independently $C_{1-4}$ alkyl or $C_{2-4}$ alkenyl, and wherein $R_{11}$ is selected from the group consisting of oxo, phenyl, toluenyl, pyrimidinyl, amino, and —O—;

wherein formula II comprises:

$$H_2N—B—D—B—NH_2 \qquad \text{II}$$

wherein "B" is a linker moiety independently selected from the group consisting of straight or branched $C_{1-6}$ alkyl, straight or branched $C_{2-6}$ alkenyl, straight or branched $C_{1-6}$ alkyl substituted with an amine moiety, and straight or branched $C_{2-6}$ alkenyl substituted with an amine moiety;

wherein "D" is a nitrogen-containing moiety selected from the group consisting of pyrimidinyl, piperidyl, pyridinyl, —CH—$CH_2$—$NH_2$, —CH—$CH_2$—$CH_2$—$NH_2$, —CH—$NH_2$, and piprazinyl;

wherein formula III comprises:

$$N\!\!\equiv\!\!C—B—D—B—D—B—C\!\!\equiv\!\!N \qquad \text{III}$$

wherein "B" and "D" are defined as in formula II.

Preferably, $R_1$ is H; $R_2$ through $R_9$ is H or $C_{1-3}$ alkyl. The preferred compounds of formula I are:

wherein the upper structure has a designation compound 38 and the bottom structure is called "214140".
The preferred compounds of formula II are:

compound 91 and compound 94. The preferred compound of formula III is:

compound 92.

The present invention further provides a method for treating a patient with cancer, comprising administering an effective amount of a compound selected from the group consisting of formula I, formula II and formula III, wherein formula I comprises:

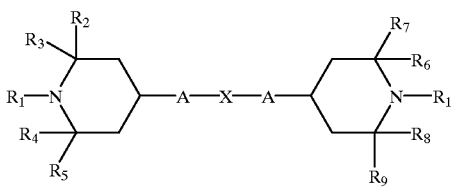
(I)

wherein "A" is independently —CH$_2$—, —O—, —NH—, —CO—, phenyl, or pyrimidnyl;

wherein R$_1$, R$_2$, R$_3$, R$_4$, R$_5$, R$_6$, R$_7$, R$_8$ and R$_9$ are each independently H, C$_{1-6}$ alkyl, C$_{1-6}$ alkenyl, C$_{1-6}$ alkoxy, or phenyl;

wherein "X" is a linker moiety selected from the group consisting of C$_{2-10}$ alkyl, C$_{2-10}$ alkenyl, and R$_{10}$–R$_{11}$=R$_{10}$; wherein R$_{10}$ is independently C$_{1-4}$ alkyl or C$_{2-4}$ alkenyl, and wherein R$_{11}$ is selected from the group consisting of oxo, phenyl, toluenyl, pyrimidinyl, amino, and —O—;

wherein formula II comprises:

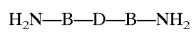

H$_2$N—B—D—B—NH$_2$        II wherein "B" is a linker moiety independently selected from the group consisting of straight or branched C$_{1-6}$ alkyl, straight or branched C$_{2-6}$ alkenyl, straight or branched C$_{1-6}$ alkyl substituted with an amine moiety, and straight or branched C$_{2-6}$ alkenyl substituted with an amine moiety;

wherein "D" is a nitrogen-containing moiety selected from the group consisting of pyrimidinyl, piperidyl, pyridinyl, —CH—CH$_2$—NH$_2$, —CH—CH$_2$—CH$_2$—NH$_2$, —CH—NH$_2$, and piprazinyl;

wherein formula III comprises:

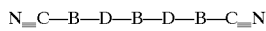

N≡C—B—D—B—D—B—C≡N        III wherein "B" and "D" are defined as in formula II.

Preferably, R$_1$ is H; R$_2$ through R$_9$ is H or C$_{1-3}$ alkyl. The preferred compounds of formula I are:

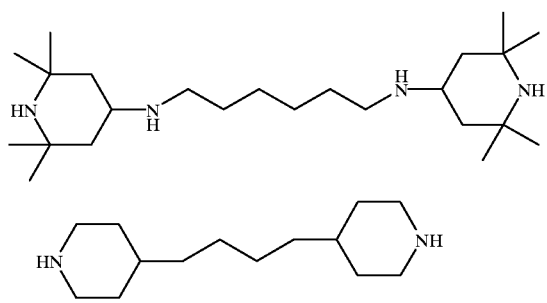

wherein the upper structure has a designation compound 38 and the bottom structure is called "214140".

The preferred compounds of formula II are:

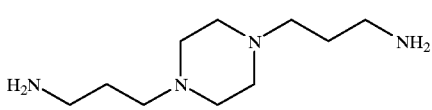

compound 91 and

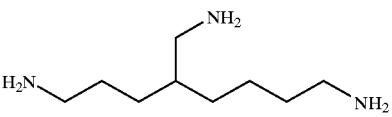

compound 94. The preferred compound of formula III is:

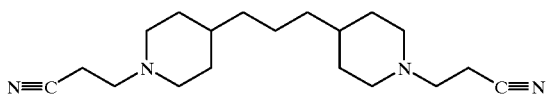

compound 92.

DETAILED DESCRIPTION OF THE INVENTION

Figure 1:
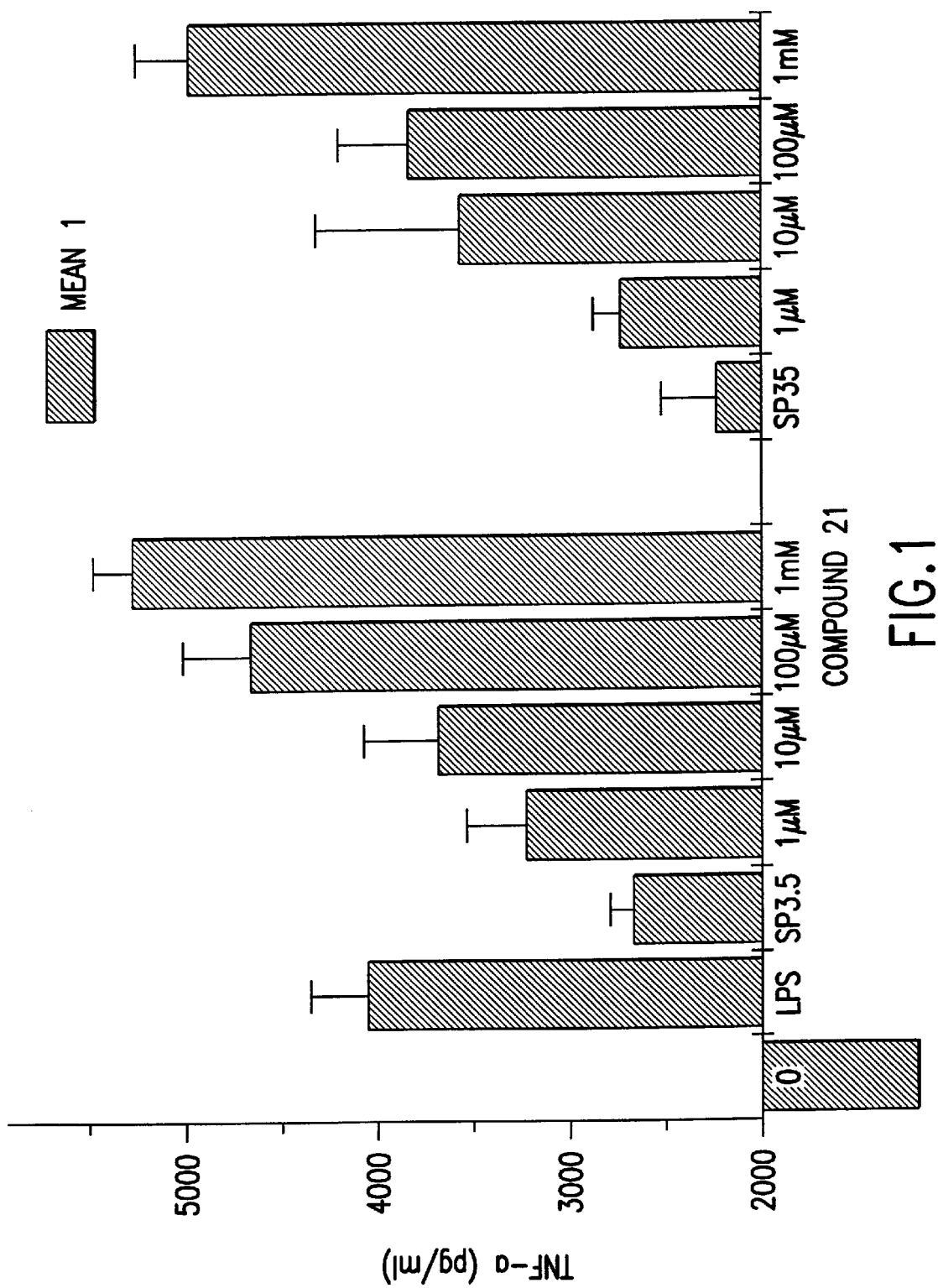
FIG. 1 shows an in vitro dose-response relationship for compound 214140 (formula I) to override the inhibitory effect of spermine on macrophage cell cultures. The measure of macrophage activation was TNF$_\alpha$ in the cell culture supernatants, as determined by commercial ELISA techniques.

The present invention provides a pharmaceutical composition for cancer immunotherapy treatment comprising a compound selected from formula I and a pharmaceutically acceptable carrier, wherein formula I comprises:

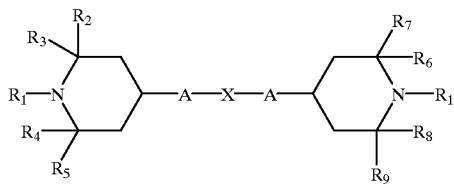

(I)

wherein "A" is independently —CH$_2$—, —O—, —NH—, —CO—, phenyl, or pyrimidnyl;

wherein R$_1$, R$_2$, R$_3$, R$_4$, R$_5$, R$_6$, R$_7$, R$_8$ and R$_9$ are each independently H, C$_{1-6}$ alkyl, C$_{1-6}$ alkenyl, C$_{1-6}$ alkoxy, or phenyl;

wherein "X" is a linker moiety selected from the group consisting of C$_{2-10}$ alkyl, C$_{2-10}$ alkenyl, and R$_{10}$–R$_{11}$=R$_{10}$; wherein R$_{10}$ is independently C$_{1-4}$ alkyl or C$_{2-4}$ alkenyl, and wherein R$_{11}$ is selected from the group consisting of oxo, phenyl, toluenyl, pyrimidinyl, amino, and —O—;

wherein formula II comprises:

H$_2$N—B—D—B—NH$_2$     II wherein "B" is a linker moiety independently selected from the group consisting of straight or branched C$_{1-6}$ alkyl, straight or branched C$_{2-6}$ alkenyl, straight or branched C$_{1-6}$ alkyl substituted with an amine moiety, and straight or branched C$_{2-6}$ alkenyl substituted with an amine moiety;

wherein "D" is a nitrogen-containing moiety selected from the group consisting of pyrimidinyl, piperidyl, pyridinyl, —CH—CH$_2$—NH$_2$, —CH—CH$_2$—CH$_2$—NH$_2$, —CH—NH$_2$, and piprazinyl;

wherein formula III comprises:

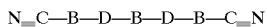     III wherein "B" and "D" are defined as in formula II.

Preferably, R$_1$ is H; R$_2$ through R$_9$ is H or C$_{1-3}$ alkyl. The preferred compounds of formula I are:

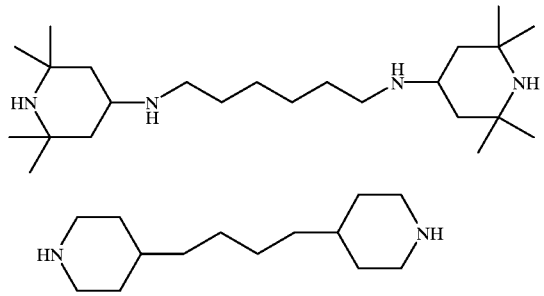

wherein the upper structure has a designation compound 38 and the bottom structure is called "214140".

The preferred compounds of formula II are:

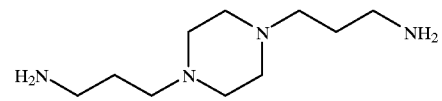

compound 91 and

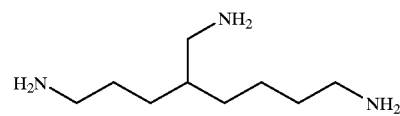

compound 94. The preferred compound of formula III is:

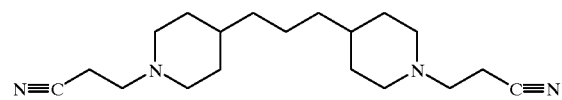

compound 92.

The present invention further provides a method for treating a patient with cancer, comprising administering an effective amount of a compound selected from the group consisting of formula I, formula II and formula III, wherein formula I comprises:

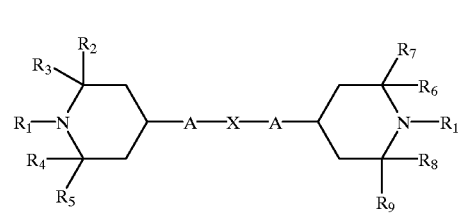

(I)

wherein "A" is independently —CH$_2$—, —O—, —NH—, —CO—, phenyl, or pyrimidnyl;

wherein $R_1$, $R_2$, $R_3$, $R_4$, $R_5$, $R_6$, $R_7$, $R_8$ and $R_9$ are each independently H, $C_{1-6}$ alkyl, $C_{1-6}$ alkenyl, $C_{1-6}$ alkoxy, or phenyl;

wherein "X" is a linker moiety selected from the group consisting of $C_{2-10}$ alkyl, $C_{2-10}$ alkenyl, and $R_{10}$–$R_{11}$=$R_{10}$; wherein $R_{10}$ is independently $C_{1-4}$ alkyl or $C_{2-4}$ alkenyl, and wherein $R_{11}$ is selected from the group consisting of oxo, phenyl, toluenyl, pyrimidinyl, amino, and —O—;

wherein formula II comprises:

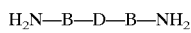
II wherein "B" is a linker moiety independently selected from the group consisting of straight or branched $C_{1-6}$ alkyl, straight or branched $C_{2-6}$ alkenyl, straight or branched $C_{1-6}$ alkyl substituted with an amine moiety, and straight or branched $C_{2-6}$ alkenyl substituted with an amine moiety;

wherein "D" is a nitrogen-containing moiety selected from the group consisting of pyrimidinyl, piperidyl, pyridinyl, —CH—CH$_2$—NH$_2$, —CH—CH$_2$—CH$_2$—NH$_2$, —CH—NH$_2$, and piprazinyl;

wherein formula III comprises:

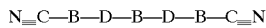
III wherein "B" and "D" are independently defined as in formula II.

Preferably, $R_1$ is H; $R_2$ through $R_9$ is H or $C_{1-3}$ alkyl. The preferred compounds of formula I are:

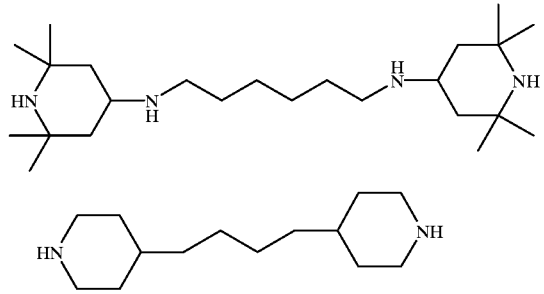

wherein the upper structure has a designation compound 38 and the bottom structure is called "214140".

The preferred compounds of formula II are:

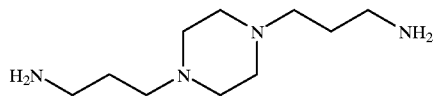

compound 91 and

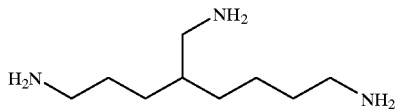

compound 94. The preferred compound of formula III is:

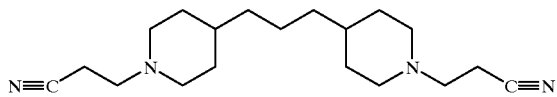

compound 92.

Each of the foregoing preferred compounds are available commercially as research reagents (Aldrich). Compound 38, for example, has industrial applications in plastics and synthetic textiles but no pharmaceutical uses.

Spermine

The pro-inflammatory cytokines TNF, IL-1, IL-6, MIP-1$_\alpha$ and MIP-1$_\beta$ play an important role in stimulating the early stages of acute inflammation, including recruitment and activation of inflammatory cells, stimulation of endothelial activation and direct cytotoxicity. These "inflammatory" cytokines play an important role for recovery from infection or injury, however, normal counter-regulatory mechanisms are also critical to the success of an immune response, because inappropriate or excessive production of pro-inflammatory cytokines can lead to shock or tissue injury. Counter-regulatory mechanism has focused upon the cytokine inhibitory roles of the glucocorticoid hormones, the anti-inflammatory cytokines, such as TGF-$_\beta$ and IL-10, and prostaglandin PGE$_2$. Specifically, local production of proinflammatory cytokines mediates a host response to inflammation, infection and injury whereas overexpression of these mediators can injure or kill the host. Spermine plays an important counter-regulatory role for pro-inflammatory cytokine production and that an excessive counter-regulatory response, mediated by excessive spermine production, can be a mechanism protecting tumors against host defense mechanisms. Thus, spermine is an important point of therapeutic intervention for imi tinotherapy of cancers, particular solid tumors, by inhibiting an excessive counter-regulatory response and allowing endogenous immune and inflammatory mechanisms to take place. Moreover, local administration of spermine in vivo protected mice against the development of acute footpad inflammation induced by carageenan.

Spermine can effectively inhibit cytokine synthesis in serum-free conditions and in the presence of the polyamine oxidase inhibitor aminoguanidine. Oxidative metabolism of spermine is not required for the counter-regulatory activity of spermine on cytokine synthesis. The spermine concentrations are readily achievable in vivo as high spermine concentrations have been reported in tumors and in patients infected with bacteria, mycobacteria and viruses (Kurihara et al., Neurosurg. 32:372–375, 1993; Susuki et al., Experimentia 40:838–839, 1984; Seiler et al., Biochem J. 225:219–226, 1985; and Cipolla et al., Eur. Urol. 24:124–131, 1993). The counter-regulatory activity of spermine also appears to act via a different cellular mechanism from that of the glucocorticoids. Others have shown that LPS stimulation of monocytes activates spermine uptake via a protein kinase C (PKC)-dependent mechanism (Khan et al., J. Cell. Physiol. 157:493–501, 1993; and Ding et al., J. Biol. Chem. 264:3924–3929, 1989) Net spermine uptake occurs following LPS stimulation in human PBMCs (peripheral blood mononuclear cells).

Immunotherapeutic Compounds

The present compounds that exhibit immunotherapeutic activity have been described structurally according to three formulae. The compounds exhibit cancer immunotherapeutic pharrnacologic activity by inhibiting spermine-induced counter-regulatory activity that tumor cells induce to protect themselves from a host defense immune response. Therefore, the inventive pharmaceutical compositions stimulate an immune response of the host against tumor cells by inhibiting an immune-inhibitory response, or a double negative makes a positive.

Tumors, particularly solid tumors, are typically found to be unafiected by macrophages capable of participating in a vigorous host immune response against the ubmor tissue. However, for the most part, these macrophages are not active (i. e., are dormant) against the invading tumor tissue. Therefore, it appears that the tumor cells are able to counter-regulate or suppress macrophage immune finctions likely by influencing an endogenous counter-regulatory mechanism, which in view of data showing high spermine concentrations in solid tumor tissue, is mediated by spermine. Therefore, it is desirable to inhibit the spermine counter-regulatory effect for therapeutic benefit.

Figure 2:
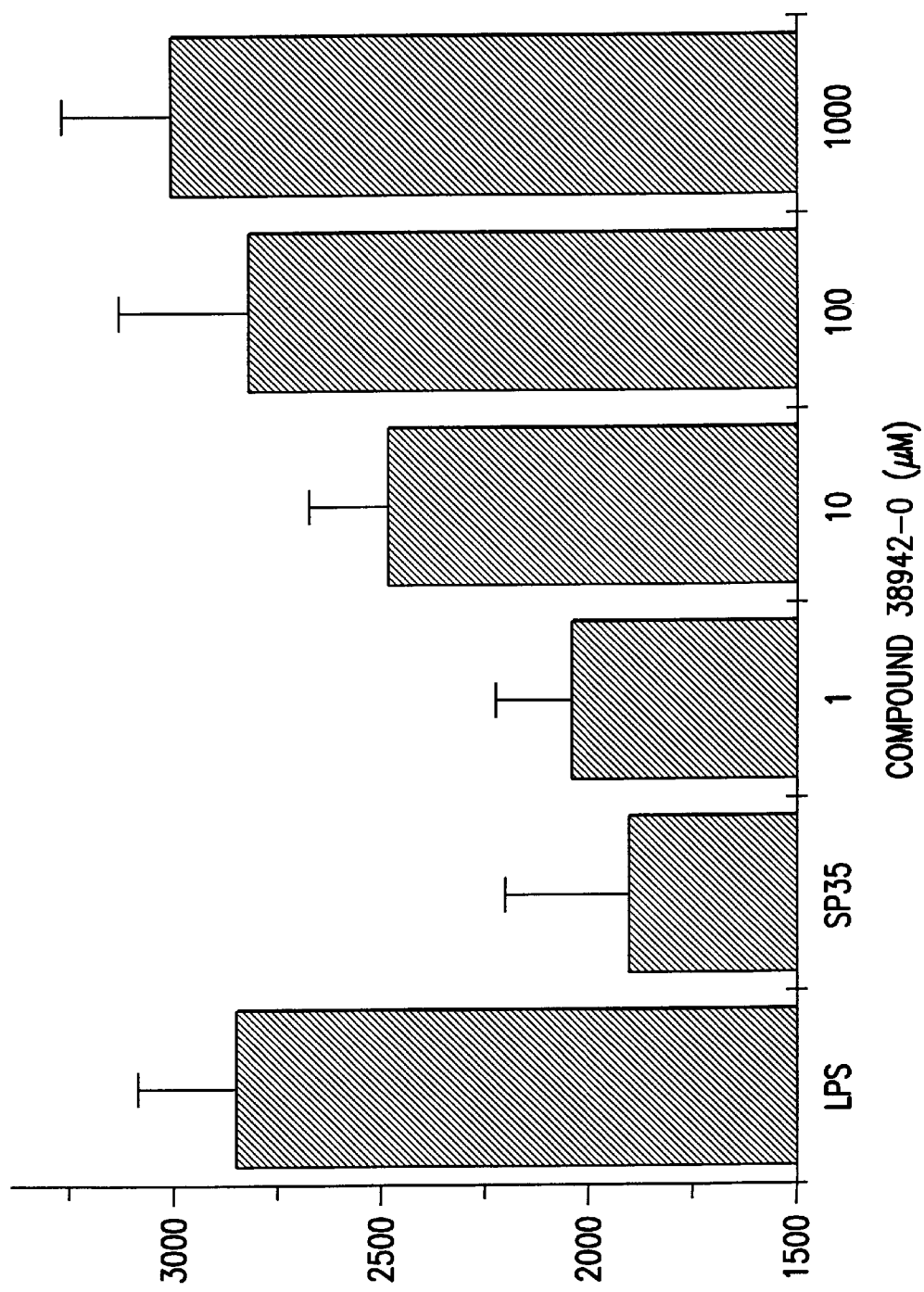
FIG. 2 shows a dose response of compound 38 (formula I) to overcome spermine inhibition of TNF$_\alpha$ release from LPS-stimulated cells.
Figure 3:
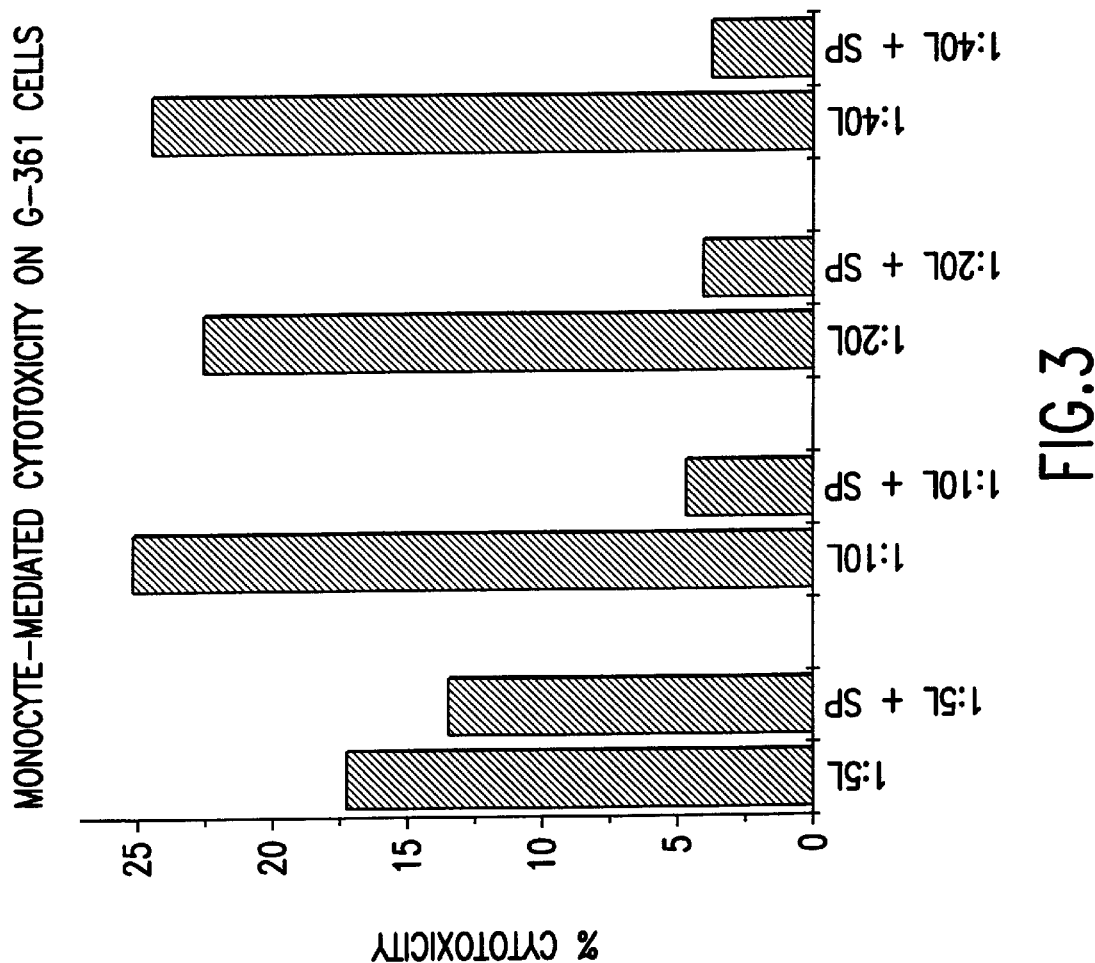
FIG. 3 shows that cellular cytotoxicity of activated monocytes (activated with 100 ng/ml of LPS) from human PBMCs (peripheral blood monocyte cultures) against G361 cells was significantly inhibited by the addition of 50–100$_\mu$M of spermine (SP).
Figure 4:
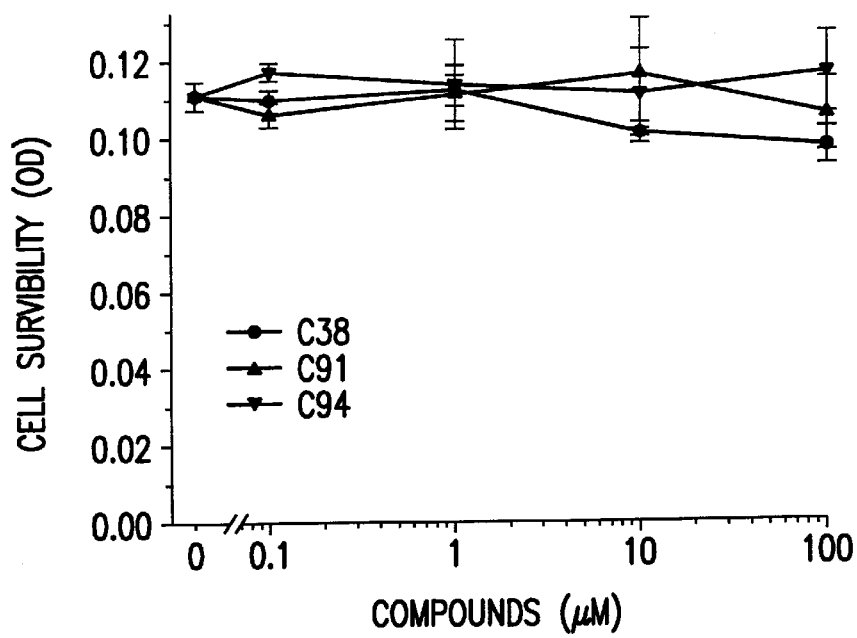
FIG. 4 shows that several of the immunomodulatory compounds (compound 38 in formula I; compound 91 in formula II; and compound 94 in formula II) that are effective immune stimulators to enhance the immune response against tumor cells are not themselves directly cytotoxic. Three of the compounds, 38, 91 and 94, at effective immunostimulatory concentrations, are not cytotoxic.

The compounds and pharmaceutical compositions found to be immunotherapeutically active, in the described in vitro assays and in an in vivo murine predictive model, exhibited anti-cancer activity by restoring the anti-tumor activity of cultured macrophage cells activated by LPS but counter-regulated by spermine. Macrophage activation was measured by release of TNF into macrophage cell culture supernatants. Compounds from each of the three formulae exhibited therapeutic activity in vitro by restoring TNF release from LPS-activated macrophage cell cultures whose activation was counter-regulated by spermine. The drug therapeutic activity was exhibited in a dose-response fashion (see FIGS. 1–2) at readily achievable plasma concentrations in vitro.

Figure 5:
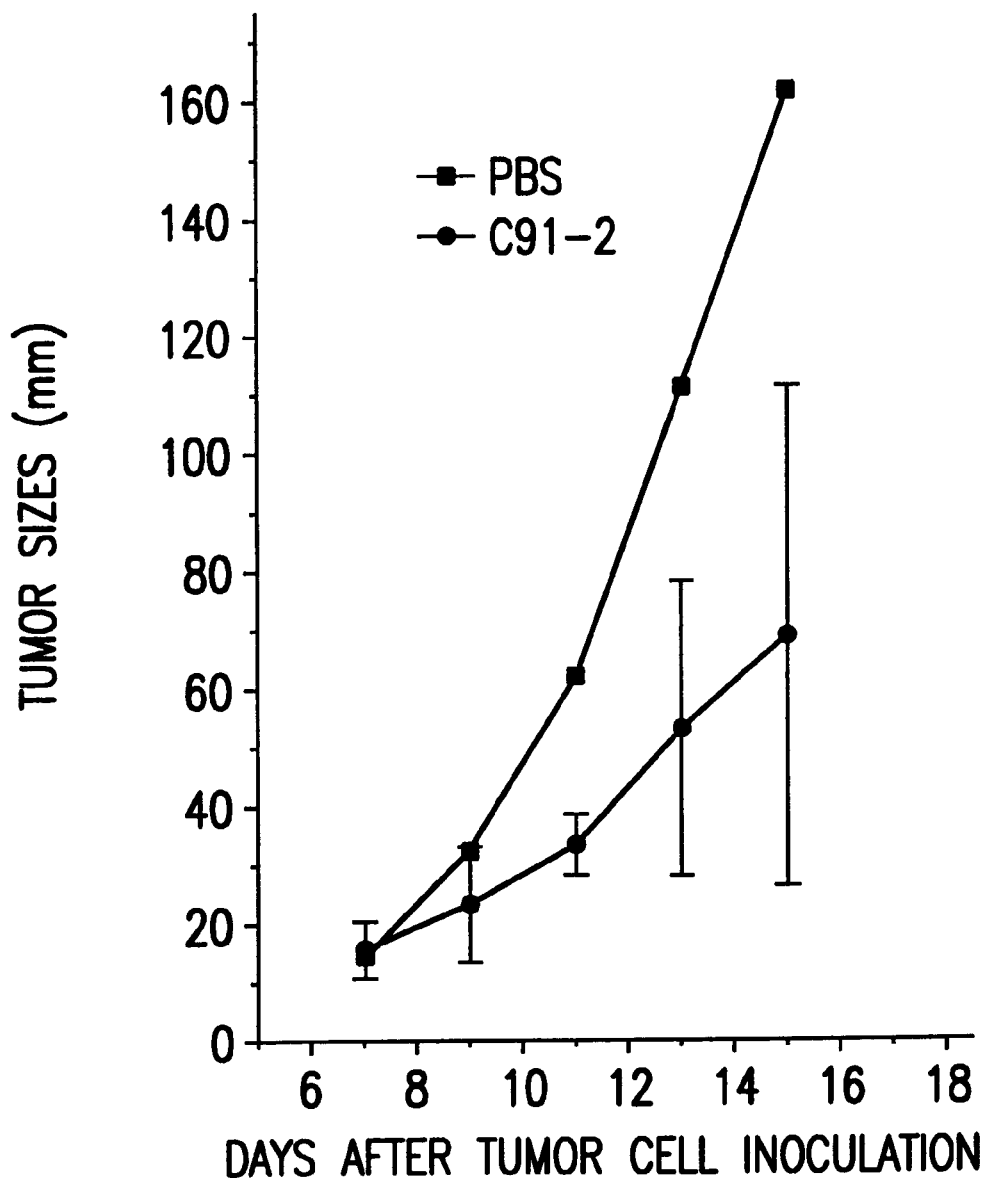
FIG. 5 shows a time-response to shrink tumor size for compound 91 (2 mg/kg) in an in vivo mouse model measuring tumor size.
Figure 6:
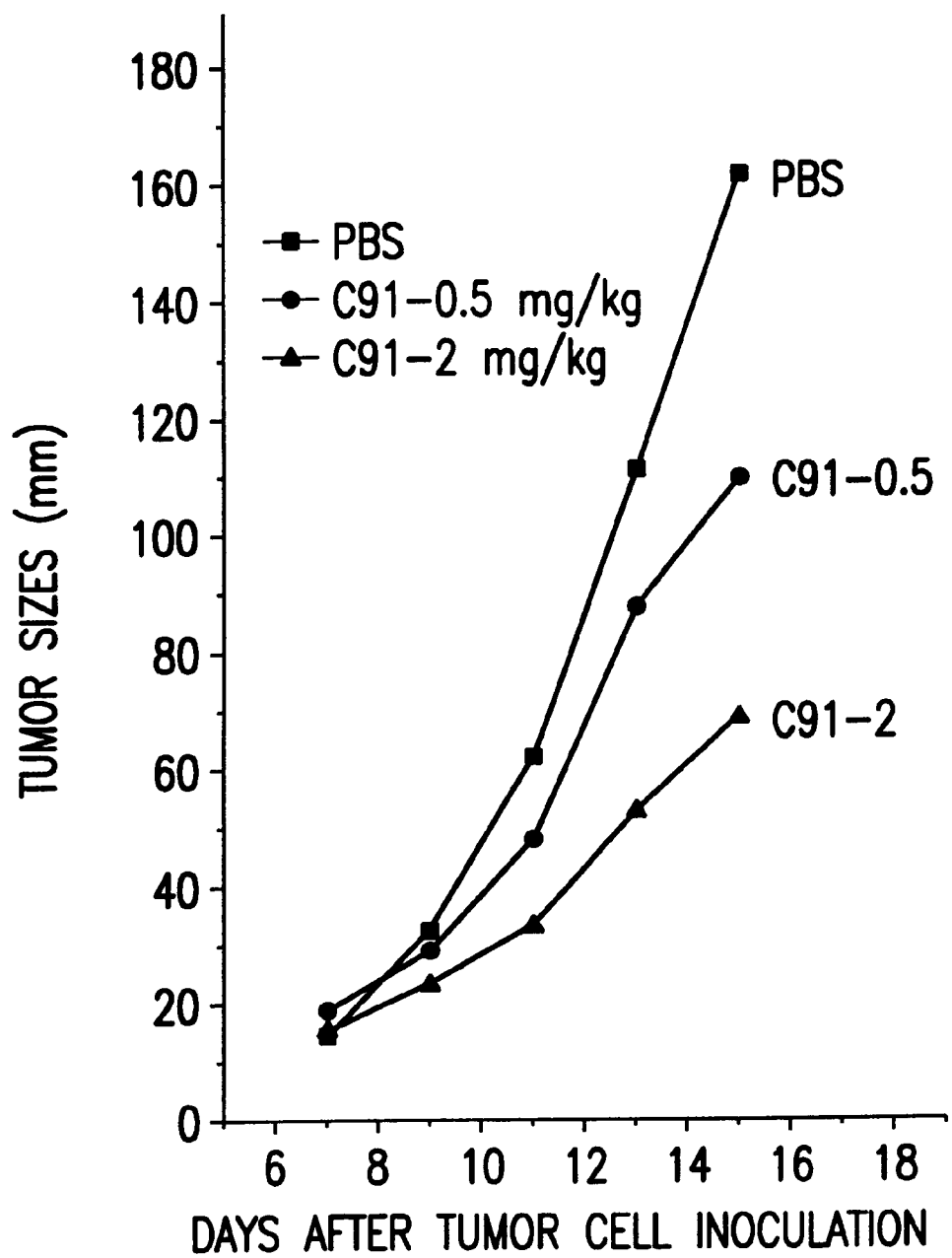
FIG. 6 shows a time response to shrink tumor size for compound 91 in an in vivo mouse model measuring tumor size at two doses (i.p.) of compound 91, 0.5 mg/kg and 2 mg/kg in a sterile PBS solution. These data show a time-response and a dose-response.
Figure 7:
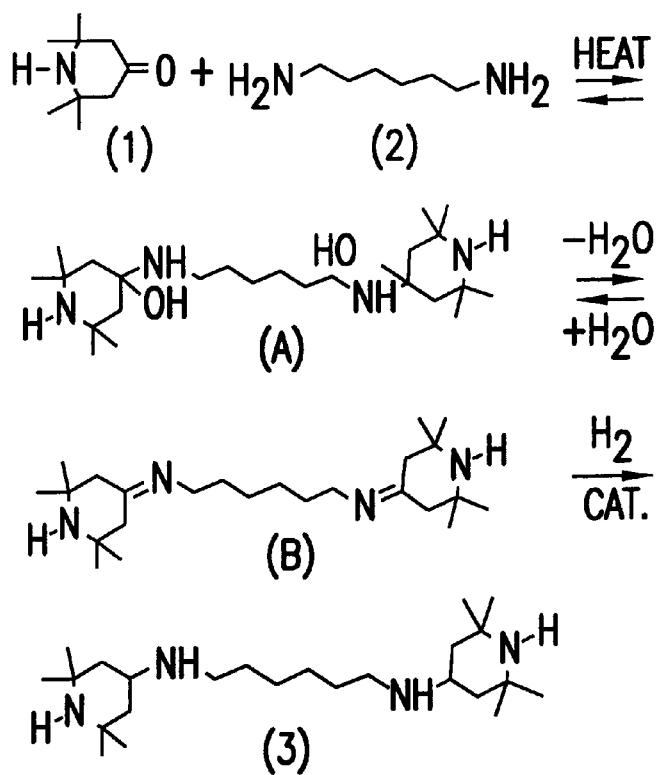
FIG. 7 shows a preferred synthesis scheme for compound 38 (N,N'-bis(2,2,6,6-tetramethyl-4-pipeidyl) hexamethylenediamine).

In addition, compounds 38 and 91 were found to shrink solid tumor masses in mice when administered parenterally (see example 3 and FIGS. 5–6). Therefore, these in vivo data in an established animal model of cancer therapy, helps to further establish the predictability of the in vitro models used for drug candidate screening.

Compound Synthesis

Figure 8:
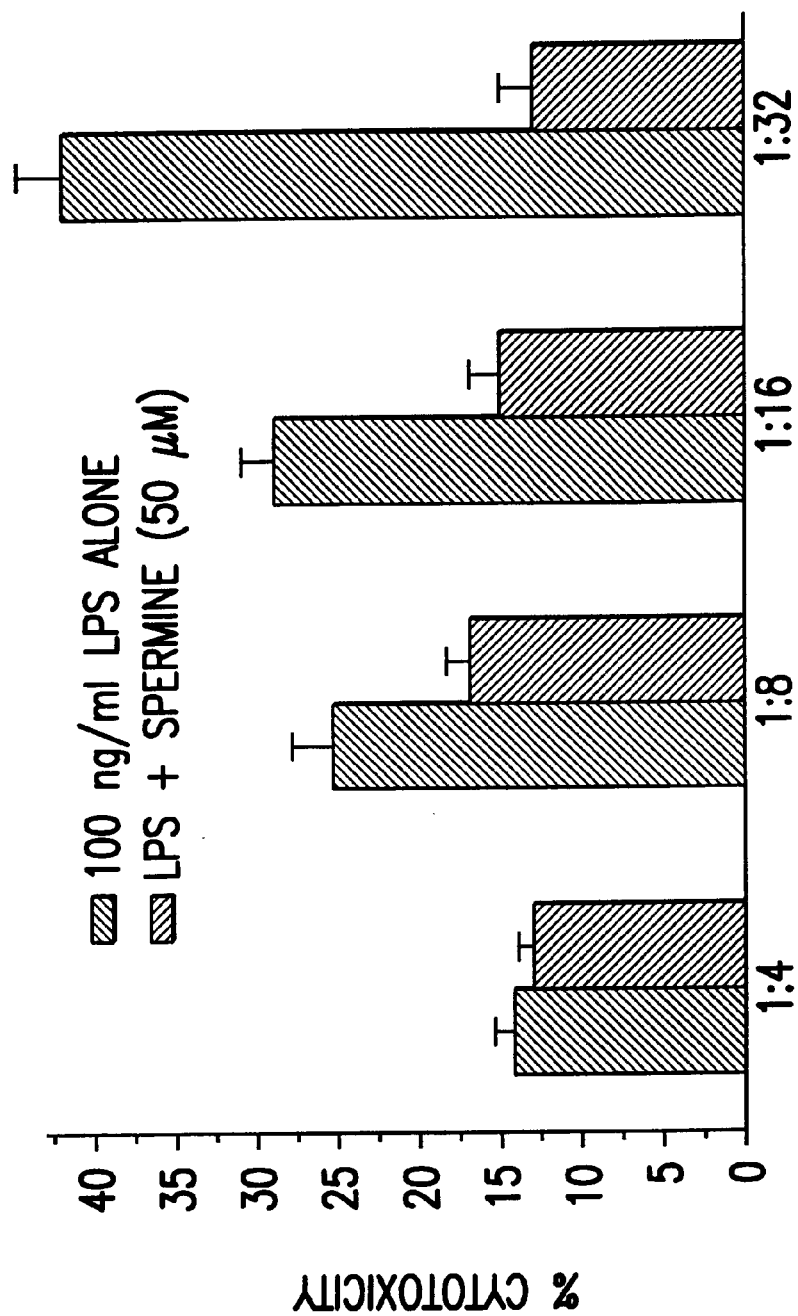
FIG. 8 shows a measure of percent cytotoxicity of 100 ng/ml LPS alone versus the same concentration of LPS with 50 mM spermine at several ratios. These data show that spermine addition reduces LPS-induced cytotoxicity.
Figure 9:
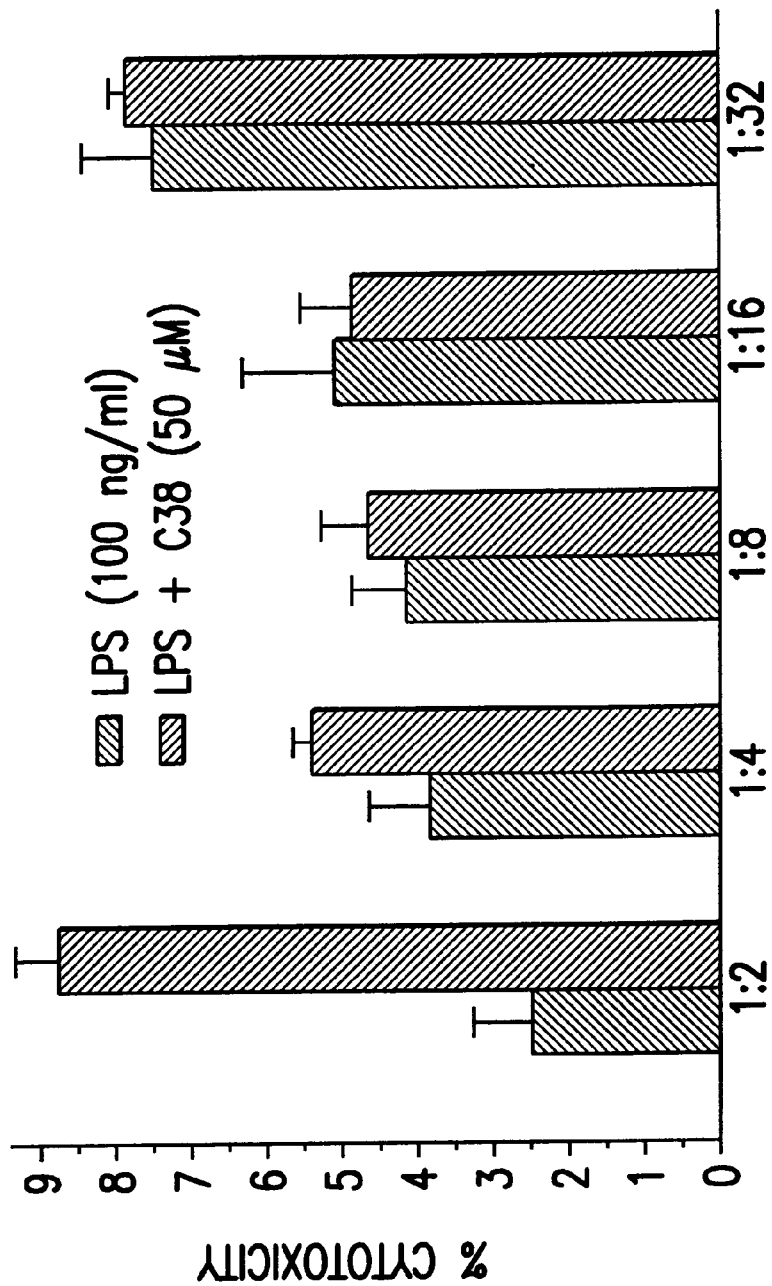
FIG. 9 shows the same experiment as reported in FIG. 8 except compound 38 is used instead of spermine. This time the addition of compound 38 has the opposite effect on cytotoxicity by increasing cytotoxicity instead of the spermine effect of reducing cytotoxicity.
Figure 10:
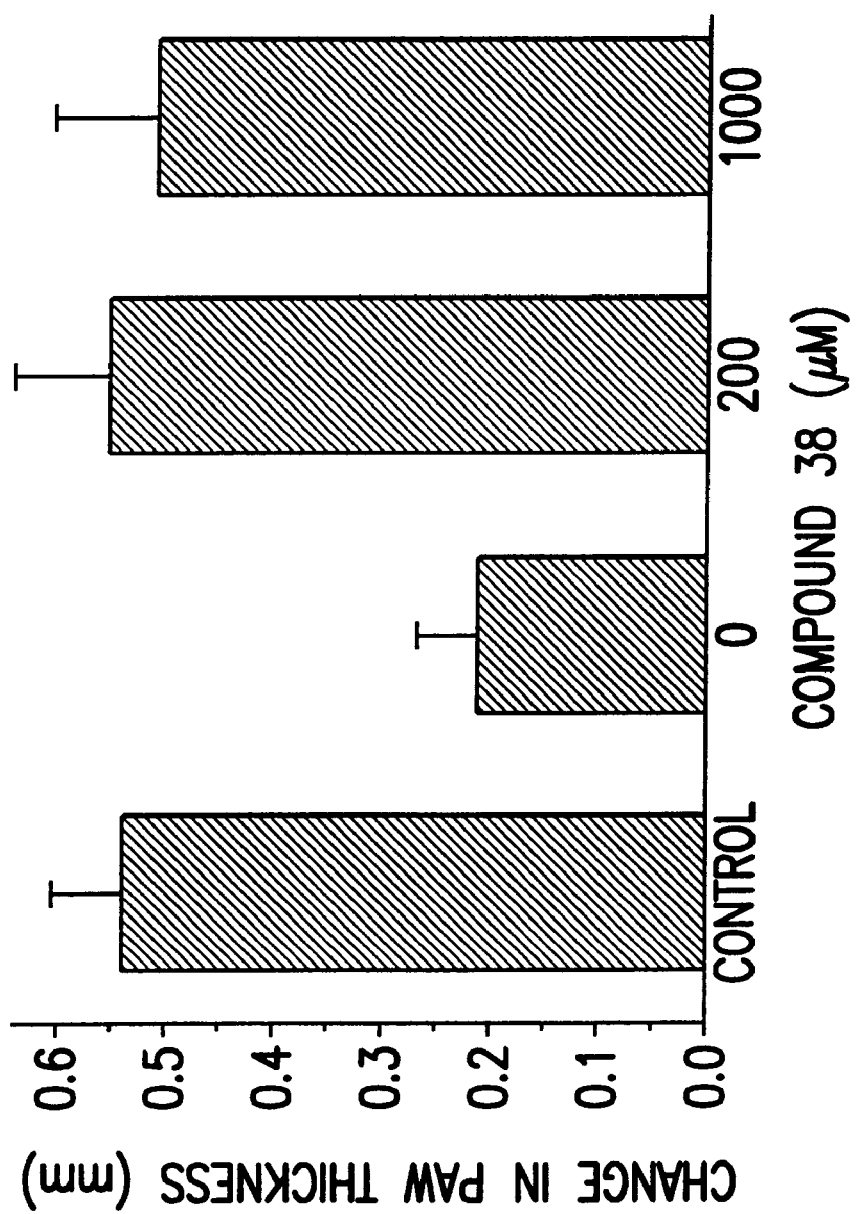
FIG. 10 shows that compound 38 at clinical concentrations overrides the spermine effect, which reduces paw thickness in a rat foot pad carageenan model of anti-inflammatory activity.
Figure 11:
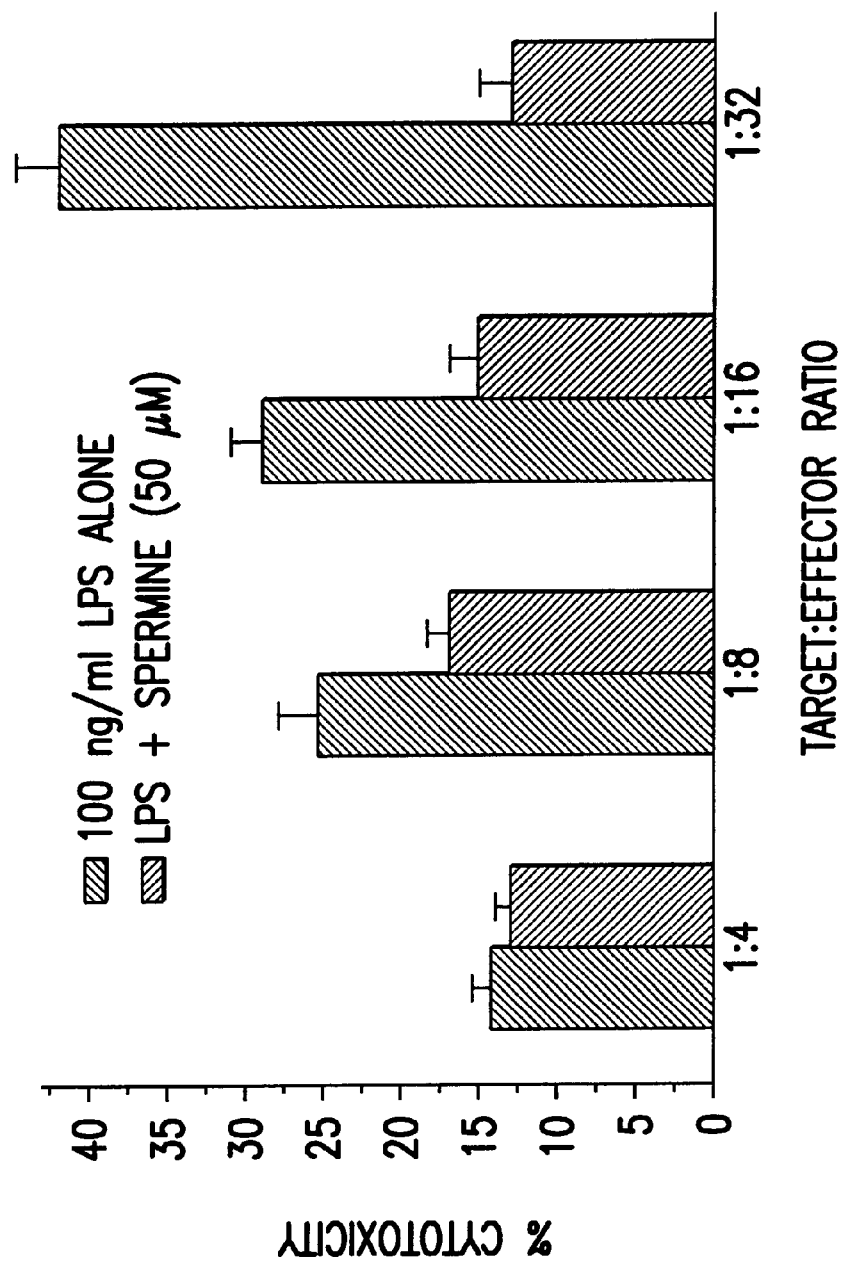
FIG. 11 shows that a concentration of 50$_\mu$M spermine effectively suppressed macrophage-mediated tumor cell killing when the macrophages were activated by endotoxin LPS).
Figure 12:
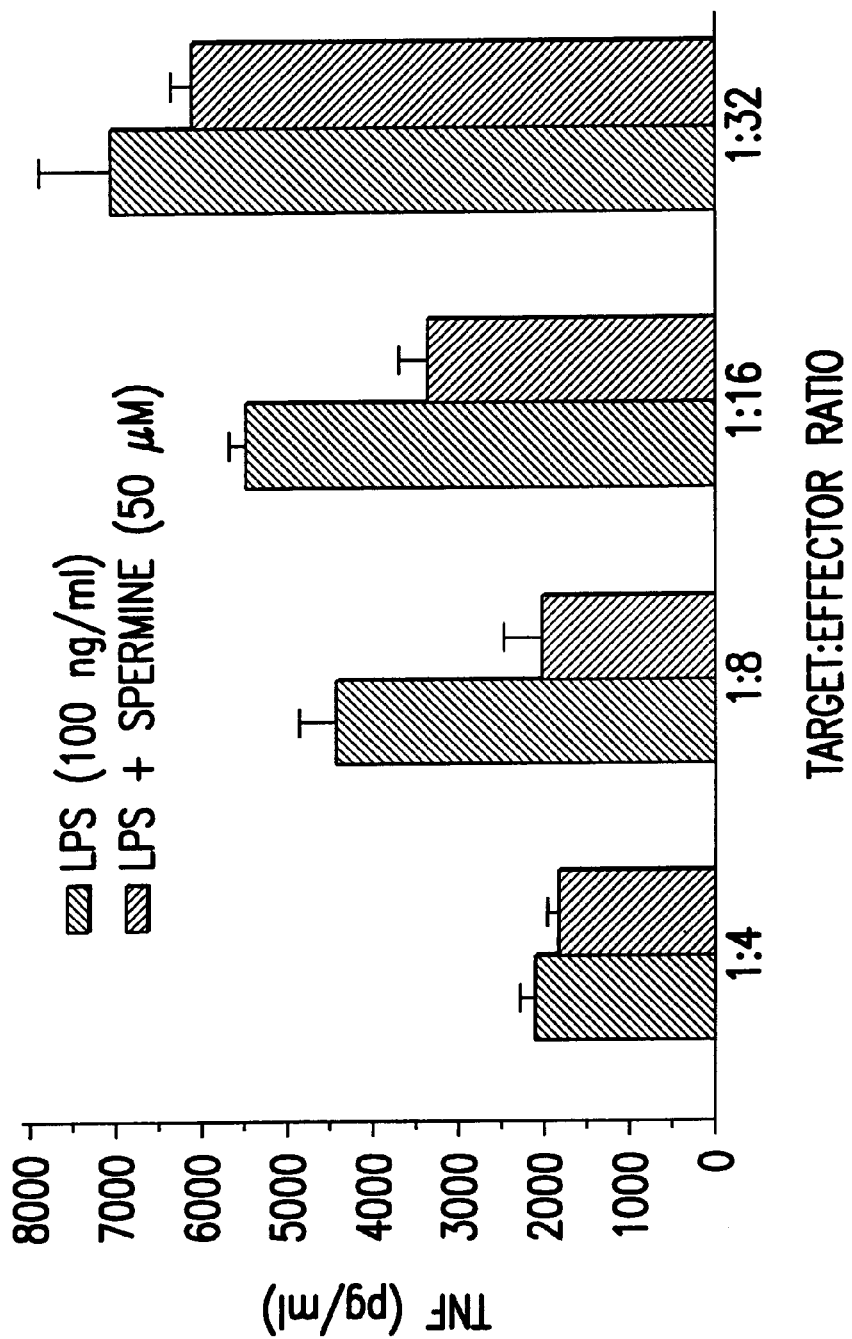
FIG. 12 shows that a concentration of 50 μM spermine effectively suppressed TNF secretion when the macrophages were activated by endotoxin (LPS).
Figure 13:
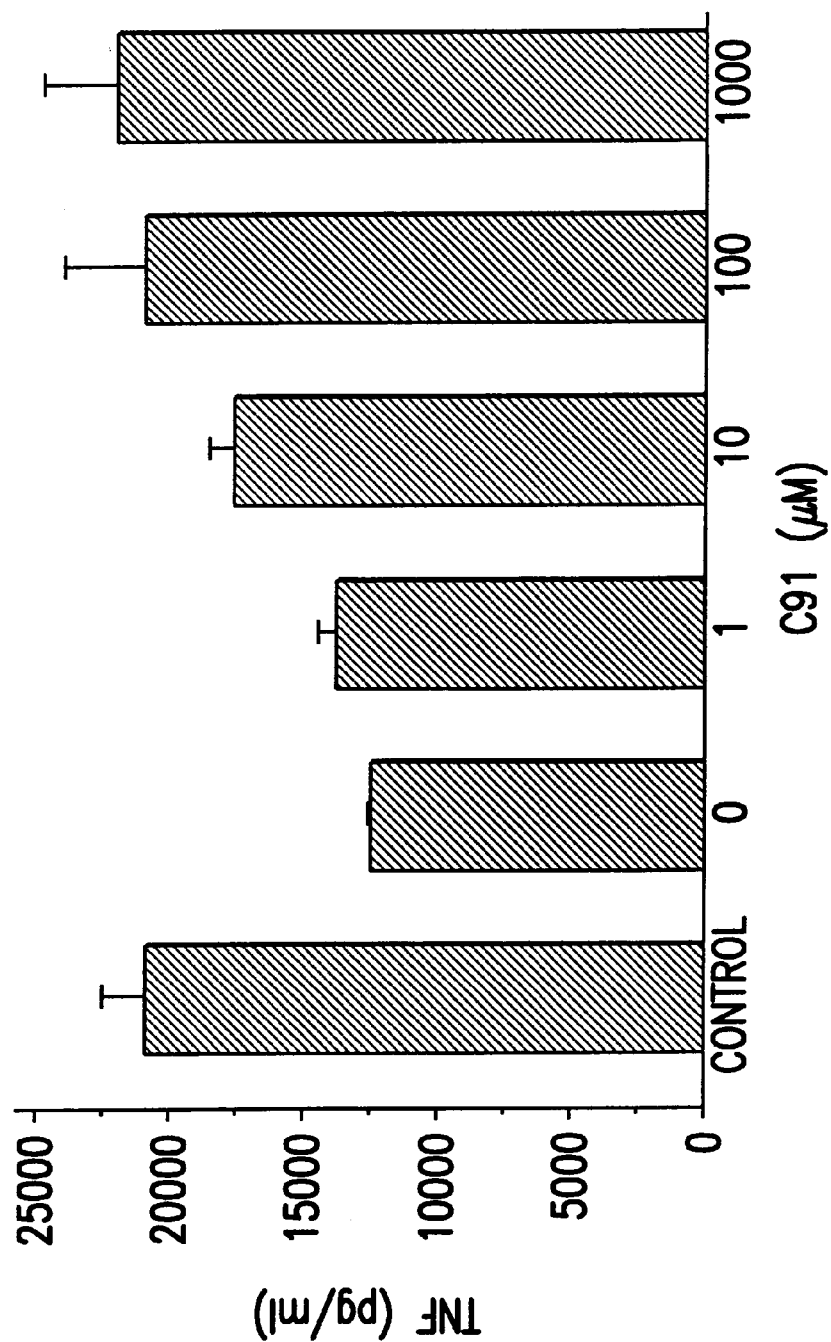
FIG. 13 shows a dose-response of compound 91 effectively overrode spermine-induced suppression of TNF secretion.
Figure 14:
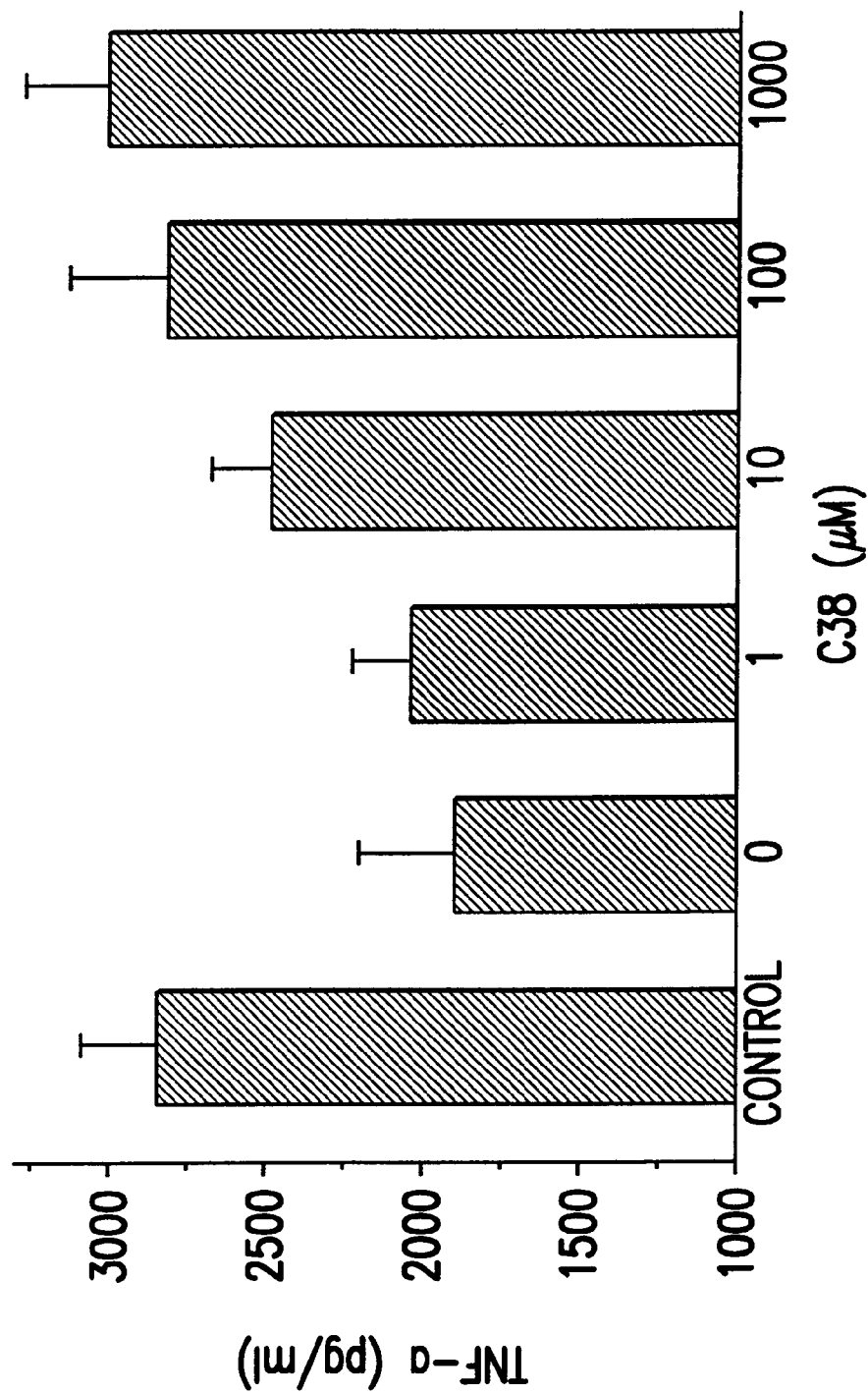
FIG. 14 shows a dose-response of compound 38 effectively overrode spermine-induced suppression of TNF secretion.
Figure 15:
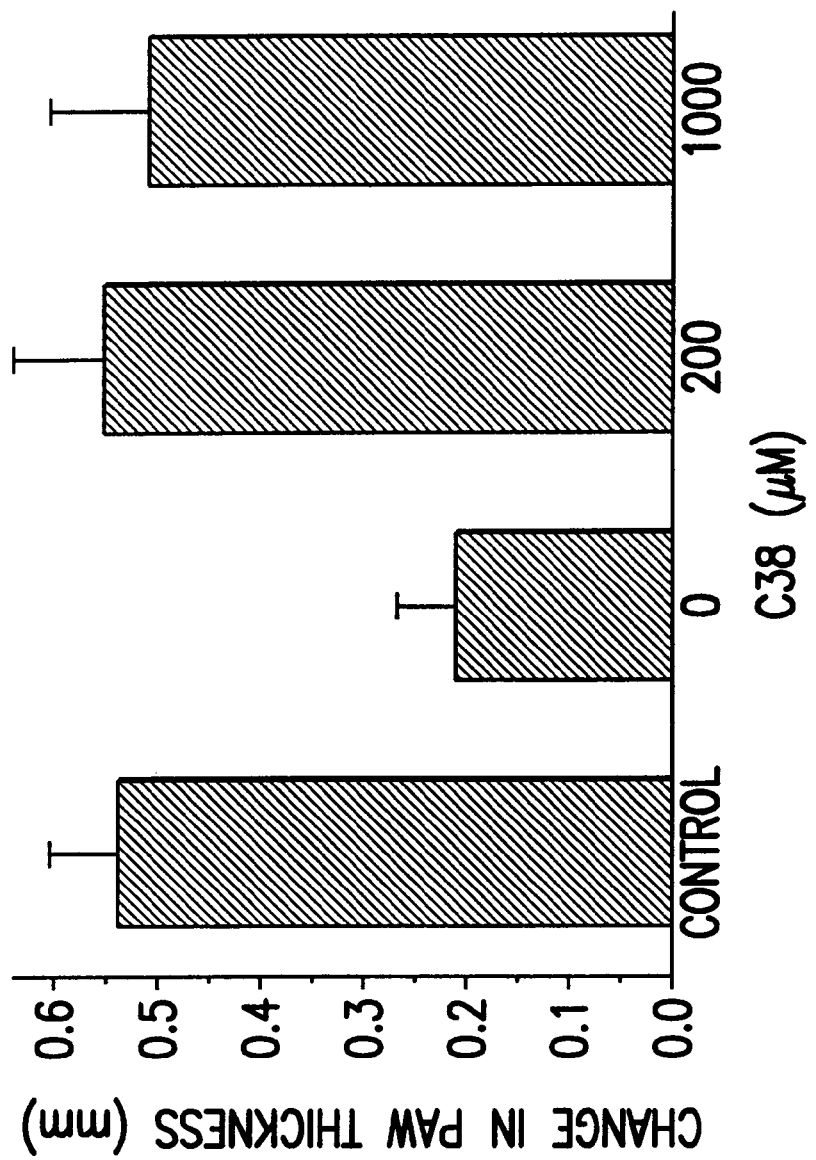
FIG. 15 shows that compound 38 overrode the inflammatory inhibition by spermine in an in vivo mouse paw edema model of inflammatory activity. Compound 38 showed a dose response to increase inflammation when inflammation was suppressed by the addition of spermine.
Figure 16:
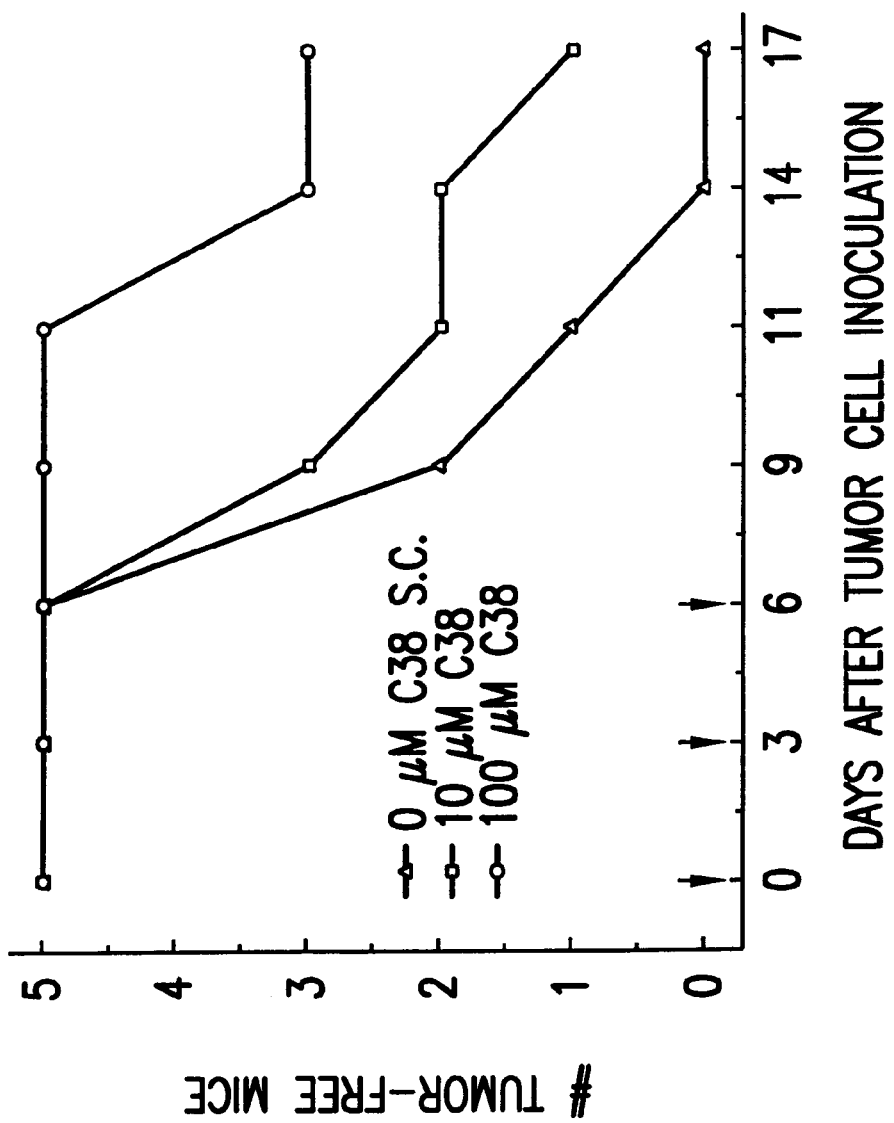
FIG. 16 shows that compound 38 treatment delayed tumor formation in mice inoculated with equal amounts of tumor cells. Three doses of compound 38 were administered at two concentrations. A dose response to compound 38 is also shown.
Figure 17:
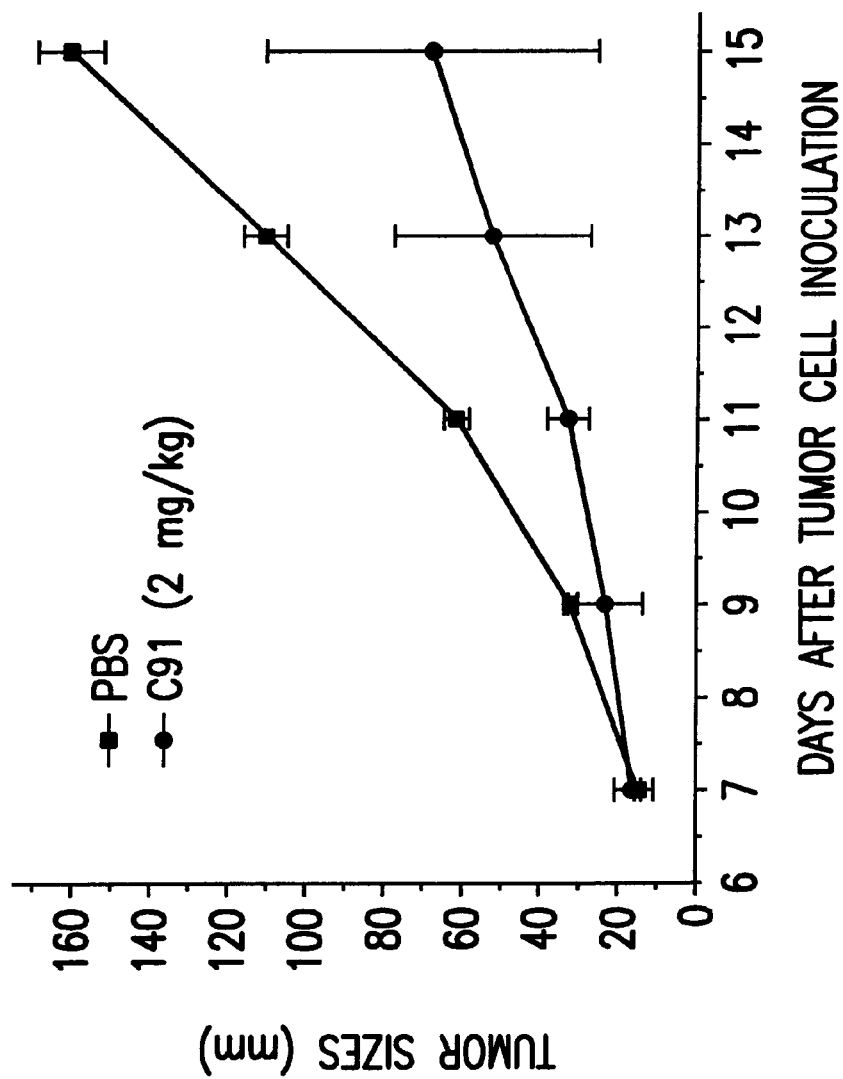
FIG. 17 shows that compound 91 inhibited the growth of established tumors in mice when the compound (2 mg/kg) was administered seven days after tumor inoculation.
Figure 18:
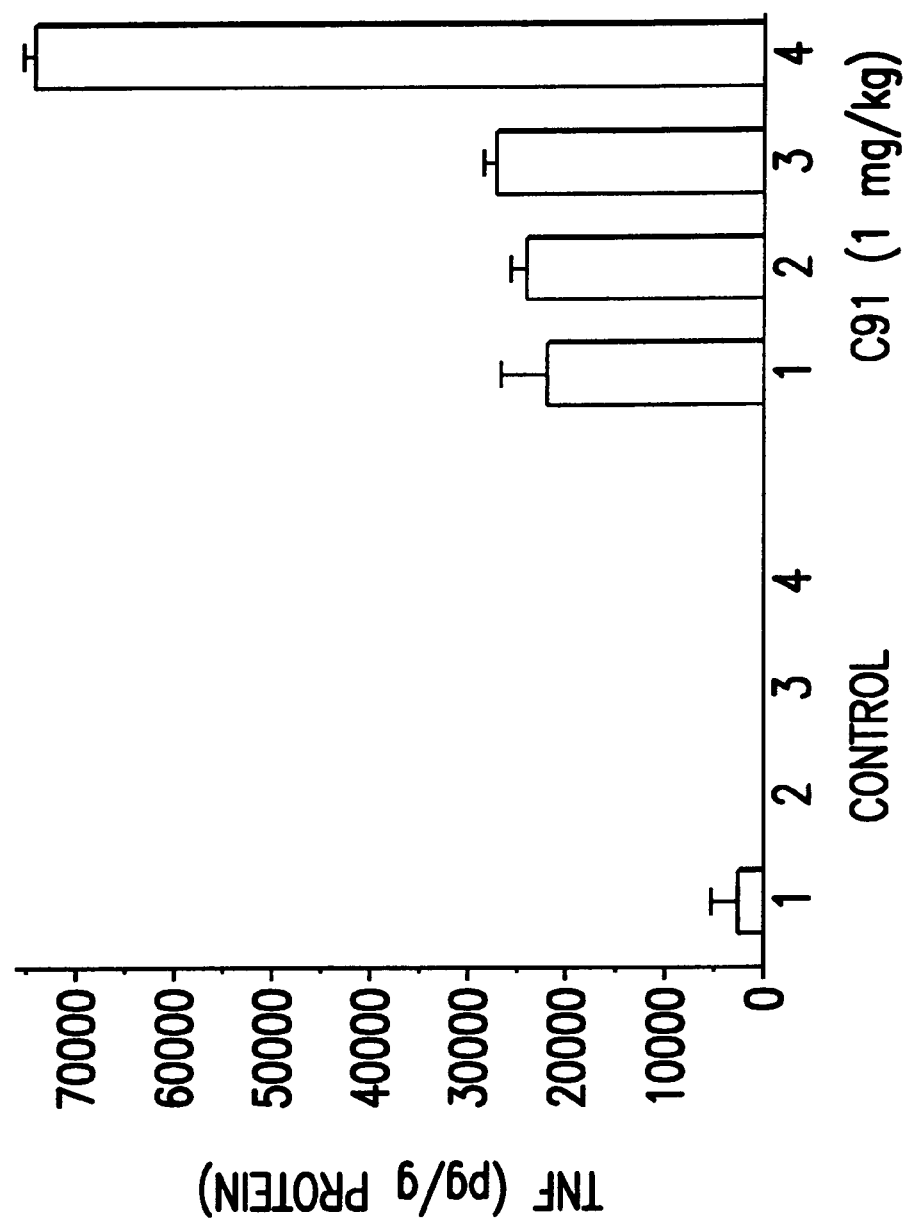
FIG. 18 shows the results of an in vivo experiment wherein solid tumor-bearing mice were administered 1 mg/kg of compound 91 and TNF levels were measured in tumor biopsy samples in four mice. These data show that compound 91 (administered ip) was able to significantly increase TNF levels in tumors to stimulate tumor immune activation.

Compound 38 is N,N'-bis(2,2,6,6-tetramethyl-4-piperidyl) hexamethylenediamine. This compound has been used as an ultraviolet stabilizer for polymeric materials. One process to synthesize compound 38 is described in Maiz et al. Chemical Industry v. 47 (*Catal. Org. React*), 369–371, Marcel Dekker, 1992. Briefly, the synthetic process involves a reductive alkylation of 2,2,6,6-tetramethyl-4-piperdone with hexamethylenediamine. This synthetic process is illustrated in FIG. 8. Crude N,N'-bis(2,2,6,6-tetramethyl-4-piperidyl) hexamethylenediamine can be synthesized with 1047 parts of 2,2,6,-tetramethyl-4-piperidone and 373 parts of hexamethylenediamine, and 2260 parts of methanol and 5.5 parts of platinum-on-carbon catalyst charged into an autoclave. The temperature of this mixture is gradually elevated from 30° C. The mixture is subject to hydrogenation at a hydro pressure of 5 kg/cm2 while the temperature is maintained at 60–70° C. It takes about 8 hours under the foregoing reaction conditions to complete the hydrogenation process. The product is filtered at about 50° C. to remove the catalyst. The filtrate is then subject to distillation to remove solvent and water formed as a by-product during the reaction. This process obtains about 1325 parts of crude N,N'-bis(2,2,6,6-tetramethyl-4-piperidyl) hexamethylenediamine having a purity of 92.9%, and an unreacted 2,2,6,6-tetramethylpiperidone content of about 0.8%. The product can be further purified by, for example crystalization. Briefly, about 100 parts of crude N,N'-bis(2,2,6,6-tetramethyl-4-piperidyl) hexamethylenediamine is added to 80 parts of acetone and the mixture heated to boiling to dissolve the N,N'-bis(2,2,6,6-tetramethyl-4-piperidyl) hexamethylenediamine. The vessel containing this mixture is cooled from the outside walls. Crystals begin to precipitate at about 29° C. Cooling is continued until the product reaches a temperature of about 5–10° C. The crystals formed are separated by filtration, washed with pure acetone, and then dried to obtain about 79.6 parts of pure N,N'-bis(2,2,6,6-tetramethyl-4-piperidyl) hexamethylenediamine having a purity of about 99.5% and good long term stability.

Pharmaceutical Formulations

Because of their pharmacological properties, the compounds of the formulae I–III can be used especially as immunotherapeutic agents to treat patients suffering from cancer. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well-known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropyhnethyl-cellulose, sodium carboxymethylcellulose, and/or polyvinylpyrrolidone (PVP). If desired, disintegrating agents may be added, such as the cross—linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLE 1

This example illustrates the in vitro TNF release screening data of several compounds and pharmaceutical compositions. Monocytes were isolated and cultured by isolating fresh human PBMCs from EDTA-blood from healthy donors (Long Island Blood Service, Melville, N.Y.) by Ficoll-Paque (Phannacia, Uppsala, Sweden) gradient. Cells were suspended in RPMI 1640 medium (Gibco BRL, Grand Island, N.Y.) containing 10% heat-inactivated human serum, 0.1% L-glutamine, and 0.01% gentamycin), and cultured at 37° C. in a humidified atmosphere of 5% $CO_2$ and 95% air. PBMCs were plated in 96-well plates at $5\times10^5$ cells per well for cytokine assay and uptake study or in 24-well plates at $5\times10^6$ cells per well for RNA study. Nonadherent cells were removed after overnight culture, and adherent cells (monocytes) were then used for experiment.

Tumor cell cultures were split tumor cells 1:3 in FBS-containing RPMI 1640 medium and incubate overnight. $20_\mu$Ci/ml$^3$H-thymidine was added to tumor cell cultures to label the cells overnight. The cells were washed to remove unabsorbed label. The cells were trypsinized and suspended in 10 ml DPBS, washed and counted. Flasks of $7.5\times10^5$, $7.5/2\times10^5$, $7.5/4\times10^5$, $7.5/8\times10^5$, $7.5/16\times10^5$ and $7.7/32\times10^5$ cells /ml in RPMI 1640 medium were prepared. The tumor cells ($200_\mu$) were added to wells containing 3×105 monocytes or control wells to make the E/T ratio 2:1, 4:1, 8:1, 16:1, 32:1 and 64:1. The cell mixture was incubated for 2 hours and macrophage-mediated cytotoxicity to tumor cells was determined.

PBMCs were isolated in a Ficoll-Paque (Phannacia) gradient and plated. After 2 hours of incubation, the nonadherent cells were removed by rinsing with RPMI 1640 medium without serum 3x, then add 25 ml human serum-containing RPMI 1640 medium with 2 ng/ml human MCSF to each 75 flask and incubate the cells overnight. The cells were labeled with 20 uCi/ml $^3$H-thymidine overnight and washed 2x with DPBS without Ca & Mg. The monocytes were isolated and counted, then diluted to $1.5\times10^6$ cells/ml in RPMI 1640. Tumor cells were diluted to $7.5\times10^5$, $7.5/2\times10^5$, $7.5/4\times10^5$, $7.5/8\times10^5$, $7.5/16\times10^5$ and $7.7/32\times10^5$ cells/ml in RPMI 1640 medium. About 200 $_\mu$l tumor cells were added at different concentration to the wells containing $3\times10^5$ monocytes or control wells to make the E/T ratio 2:1, 4:1, 8:1, 16:1, 32:1 and 64:1, then incubated for 2 hrs.

About 400 $_\mu$g/$_\mu$l LPS was sonicated for 10 min, then 19.2 $_\mu$l 400 $_\mu$g/ml LPS was added to 10 ml RPMI 1640 medium. If compounds such as spermine or/and C38 used, 15.3 (7.66) $_\mu$l of 50 mM spermine or/and 50 mM C38was added to 1 ml medium with LPS to make final concentration to 100 (50) $_\mu$M. 30 $_\mu$l of LPS solution (without or with spermine orland C38) was added to each well and incubated for 40–48 hours.

Monocytes were activated to release cytokines by treating cells with 100 ng/ml sonicated LPS (Sigma, St. Louis, Mo.) and 25 u/ml recombinant human interferon-$_\gamma$ (Boehringer Mannheim, Mannheim, Germany) except 1 $_\mu$g/ml LPS alone for IL-1$_\beta$. For treating cells with spermine, cells were pretreated with spermine (Sigma, St. Louis, Mo.) one hour before LPS/IFG stimulation. Spermine was made freshly each time in sterile-filtered deionized water at 51.2 mM or 35 mM, and then diluted in complete RPMI 1640 medium followed by adding to individual wells to yield the fmal concentration indicated. Control wells received an equal volume of medium only were used in all experiment. A lactate dehydrogenase (LDH) assay indicated that spermine at the concentrations indicated did not affect cell viability significantly.

To determine an inflammatory rat foot pad edema model with carrageenan, female C3H/HeN mice (20–25g) were obtained from Jackson Laboratories, and 5 mice were used in each group to obtain statistically significant results. Carrageenan (Sigma, St. Louis, Mo.) was made in PBS at 37° C. 3 days or more before using. Spermine (Sigma, St. Louis, Mo.) was made freshly each time. Carrageenan (50 $_\mu$l, 0.2%) was injected into the plantar surface of the left hind paw to induce paw edema in control group, and spermine at the doses indicated was coadministered in 50 $_\mu$l PBS in three spermine groups. The right hind paw was injected with the same volume of PBS as control for every groups. The thickness of the two paws was measured double-blindly using a caliper 3 hours and 28 hours later. The difference in the thickness between the two paws was taken as inflammatory index.

In order to determine antitumor therapeutic activity in vivo, mice were shaved (on their backs), B16 Fl tumor cells from 175 mm flask with 80% confluent cells and suspend the cells in 5 ml 1x DPBS were collected. Different concentrations of drug (compound 38) were prepared to provide final concentrations of 0 $_\mu$M, 50 $_\mu$M, 250 $_\mu$M and 500 $_\mu$M, by adding 50 mM of a compound 38 solution to B16 cells ($10^6$ cells/ml DPBS), nothing to 0 tube with 2 ml cells, 20 $_\mu$l to 500 $_\mu$M tube with 2 ml cells, 10 $_\mu$l to 250 $_\mu$M tube with 2 ml cells, and then transfer 0.25 ml of mixture from 250 $_\mu$M tube to 50 $_\mu$M tube with 1 ml cells. Approximately 100 $_\mu$l of cells ($10^5$) were injected with or without compound 38 into each animal S.C. in the left back region, 5 mice per group. The mice were divided according to the following groups: Group 1 $10^5$ B16 cells; Group 2 $10^5$ B16 cells plus 50 $_\mu$M compound 38 and the same amount of compound 38 on days 3 and 6; Group 3 $10^5$ B16 cells plus 250 $_\mu$M compound 38 and the same amount of compound 38 on days 3 and 6; Group 4 $10^5$ B16 cells plus 500 $_\mu$M compound 38 and the same amount of compound 38 on days 3 and 6; Group 5 $10^5$ B16 cells plus 250 $_\mu$M compound 38 and also on days 3 and 6; and Group 6 $10^5$ B16 cells plus 500 $_\mu$M compound,38 compound 38 and also on days 3 and 6.

In a second experiment of compound 38 of five mice per group wherein the cells and compound were injected by either sc or ip administration, the groups were as follows: Group 1 1×DPBS S.C. 50 μl; Group 2 100 μM compound 38 S.C. 50 μl; Group 3 500 μM compound 38 S.C. 50 μl; Group 4 1000 μM compound 38 S.C. 50 μl; Group 5 500 μM compound 38 I.P. 50 and Group 6 1000 μM compound 38 I.P. 50 μl.

During the in vivo experiments, we observed a ratio-dependent tumor cell killing mediated by macrophages; modulation of TNF synthesis in macrophages by tumor cells; identification of tumor cell-derived macrophage inactivator.

We claim:

1. A method for treating a patient with cancer, said cancer being susceptible to macrophage deactivation by spermine, comprising administering an effective amount of a compound selected from the group consisting of formula I, formula II and formula III, wherein formula I comprises:

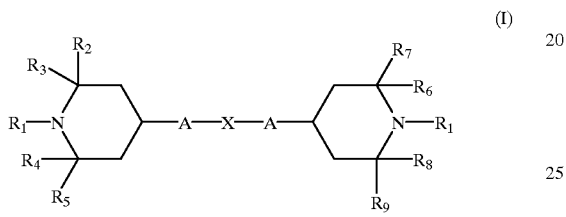
(I)

wherein "A" is independently —$CH_2$—, —O—, —NH—, —CO—, phenyl, or pyrimidnyl;

wherein $R_1$, $R_2$, $R_3$, $R_4$, $R_5$, $R_6$, $R_7$, $R_8$ and $R_9$ are each independently H, $C_{1-6}$ alkyl, $C_{1-6}$ alkenyl, $C_{1-6}$ alkoxy, or phenyl;

wherein "X" is a linker moiety selected from the group consisting of $C_{2-10}$ alky, $C_{2-10}$ alkenyl, and $R_{10}$–$R_{11}$= $R_{10}$; wherein $R_{10}$ is independently $C_{1-4}$ alkyl or $C_{2-4}$ alkenyl, and wherein $R_{11}$ is selected from the group consisting of CO—CH=, —$CH_2$-phenyl-CH=, —$CH_2$-toluenyl-CH=, —$CH_2$- pyrimidinyl- CH=, and —$CH_2$—O—CH=;

wherein formula II comprises:

II wherein "B" is a linker moiety independently selected from the group consisting of straight or branched $C_{1-6}$ alkyl, straight or branched $C_{2-6}$ alkenyl, straight or branched $C_{1-6}$ alkyl substituted with an amine moiety, and straight or branched $C_{2-6}$ alkenyl substituted with an amine moiety;

wherein "D" is a nitrogen-containing moiety selected from the group consisting of pyrimidinyl, piperidyl, pyridinyl, —CH—$CH_2$—$NH_2$, —CH—$CH_2$—$CH_2$—$NH_2$, —CH—$NH_2$, and piprazinyl;

wherein formula III comprises:

III wherein "B" and "D" are independently defined as in formula II.

2. The method of claim 1 wherein $R_1$ is H.

3. The method of claim 1 wherein $R_2$ through $R_9$ is H or $C_{1-3}$ alkyl.

4. The method of claim 1 wherein the compound of formula II is

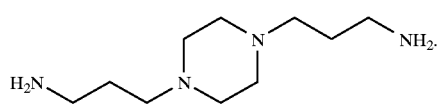

5. The method of claim 1 wherein the compound of formula II is

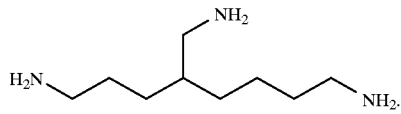

6. The method of claim 1 wherein the compound of formula III is

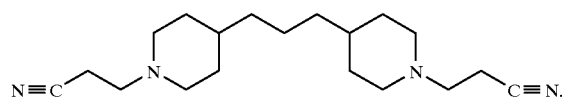

* * * * *